US00PP34420P2

(12) United States Plant Patent
MacGregor et al.

(10) Patent No.: US PP34,420 P2
(45) Date of Patent: Jul. 12, 2022

(54) GEUM PLANT NAMED 'MACGEU007'

(50) Latin Name: ***Geum coccineum* Sm. x *G. quellyon* Sweet (syn. *G. chiloense* hort.)**
Varietal Denomination: 'MACGEU007'

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 17/300,899

(22) Filed: Dec. 13, 2021

(30) Foreign Application Priority Data

Dec. 11, 2020 (QZ) ..... PBR 2020/3275

(51) Int. Cl.
*A01H 5/02* (2018.01)
*A01H 6/00* (2018.01)
*A01H 6/74* (2018.01)

(52) U.S. Cl.
USPC ..... Plt./263.1
CPC ..... *A01H 6/00* (2018.05); *A01H 6/74* (2018.05)

(58) Field of Classification Search
USPC ..... Plt./263.1
CPC ..... A01H 6/74
See application file for complete search history.

*Primary Examiner* — Anne Marie Grunberg
(74) *Attorney, Agent, or Firm* — Samuel R. McCoy, Jr.

(57) ABSTRACT

'MACGEU007' is a new and distinctive variety of *Geum* plant which is characterized by a freely-branched habit with an abundance of foliage and a broad vase shape profile, an abundance of flowering stems with large compound cymes, each bearing many vibrant orange semi-doubled flowers, and a long bloom period. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Geum coccineum* Sm. x *G. quellyon* Sweet (syn. *G. chiloense* hort.).

Variety denomination: The inventive variety of *Geum* hybrid disclosed herein has been given the variety denomination 'MACGEU007'.

CROSS REFERENCE TO RELATED APPLICATIONS

This application claims priority to the Community Plant Variety Rights application number 2020/3275, filed Dec. 11, 2021, which is herein incorporated by reference.

BACKGROUND OF THE INVENTION

Parentage: 'MACGEU007' is the result of a controlled cross-pollination breeding program carried out by the inventors at their commercial nursery in Kirkcudbright, Scotland, in the early summer of 2015. The inventors performed a controlled cross-pollination of the emasculated seed parent, *Geum chiloense* 'Blazing Sunset' (unpatented), with *Geum coccineum* 'Eos Hybrid No. 1' (unpatented), the pollen parent, which is a cultivar developed and owned by the inventors and never released to the public. Said pollination was performed in an insect proof environment. Seed from said cross was harvested, then germinated, and the resulting seedlings were then grown to a mature size in a protected poly tunnel greenhouse. In the summer of 2016, the inventors first observed the new *Geum* cultivar and noted it for its unique flower and bloom characteristics. Upon further observation to confirm the uniqueness and stability of the characteristics first observed, the new variety was selected for commercialization in the summer of 2017. This new and distinctive cultivar was given the name 'MACGEU007'.

Asexual Reproduction: Asexual reproduction of 'MACGEU007' was first accomplished in the late summer of 2017 by way of vegetative division Kirkcudbright, Scotland, and subsequently by way of meristematic tissue culture micro propagation at a laboratory in Rijswijk, the Netherlands. Successive generations have shown that the unique features of the instant cultivar are stable and reproduce true to type.

SUMMARY OF THE INVENTION

The cultivar 'MACGEU007' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geum* cultivar, 'MACGEU007'.

1. *Geum* 'MACGEU007' exhibits a freely-branched habit with an abundance of foliage and a broad vase shape profile; and
2. *Geum* 'MACGEU007' exhibits an abundance of flowering stems with large compound cymes, each bearing many vibrant orange semi-doubled flowers; and 3. *Geum* 'MACGEU007' exhibits a long bloom period, with repeat flowering from early spring and into autumn in Kirkcudbright, Scotland.

BOTANICAL DESCRIPTION OF THE PLANT

Figure 1:
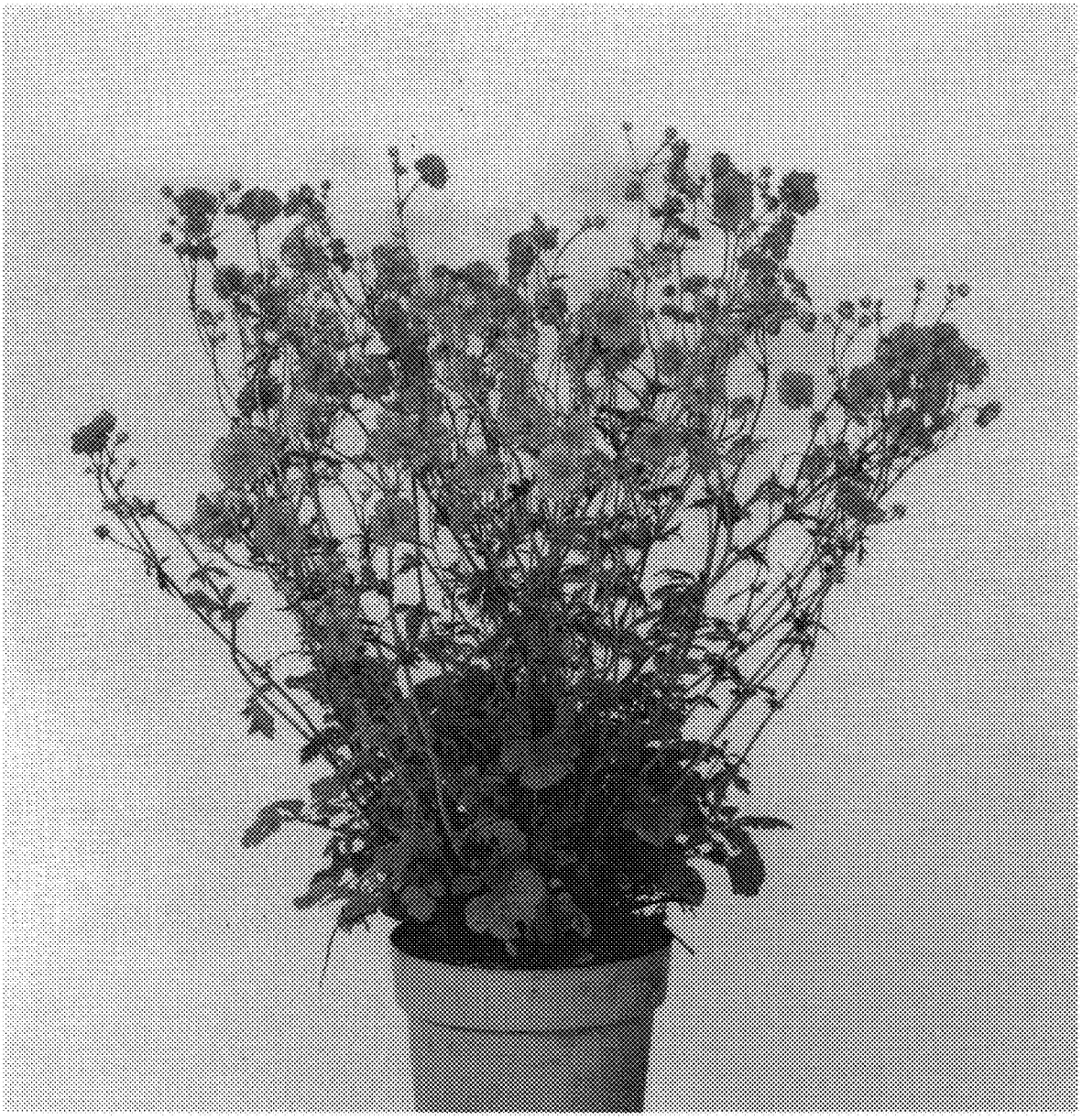
FIG. 1 shows, as nearly true as it is reasonably possible to make the same in color illustrations of this type, the typical foliage and growth characteristics of the new cultivar, 'MACGEU007'. The plant shown is approximately 4.5-month-old, potted into a 3 liter nursery pot, grown outdoors in Kirkcudbright, Scotland at a commercial nursery.
Figure 2:
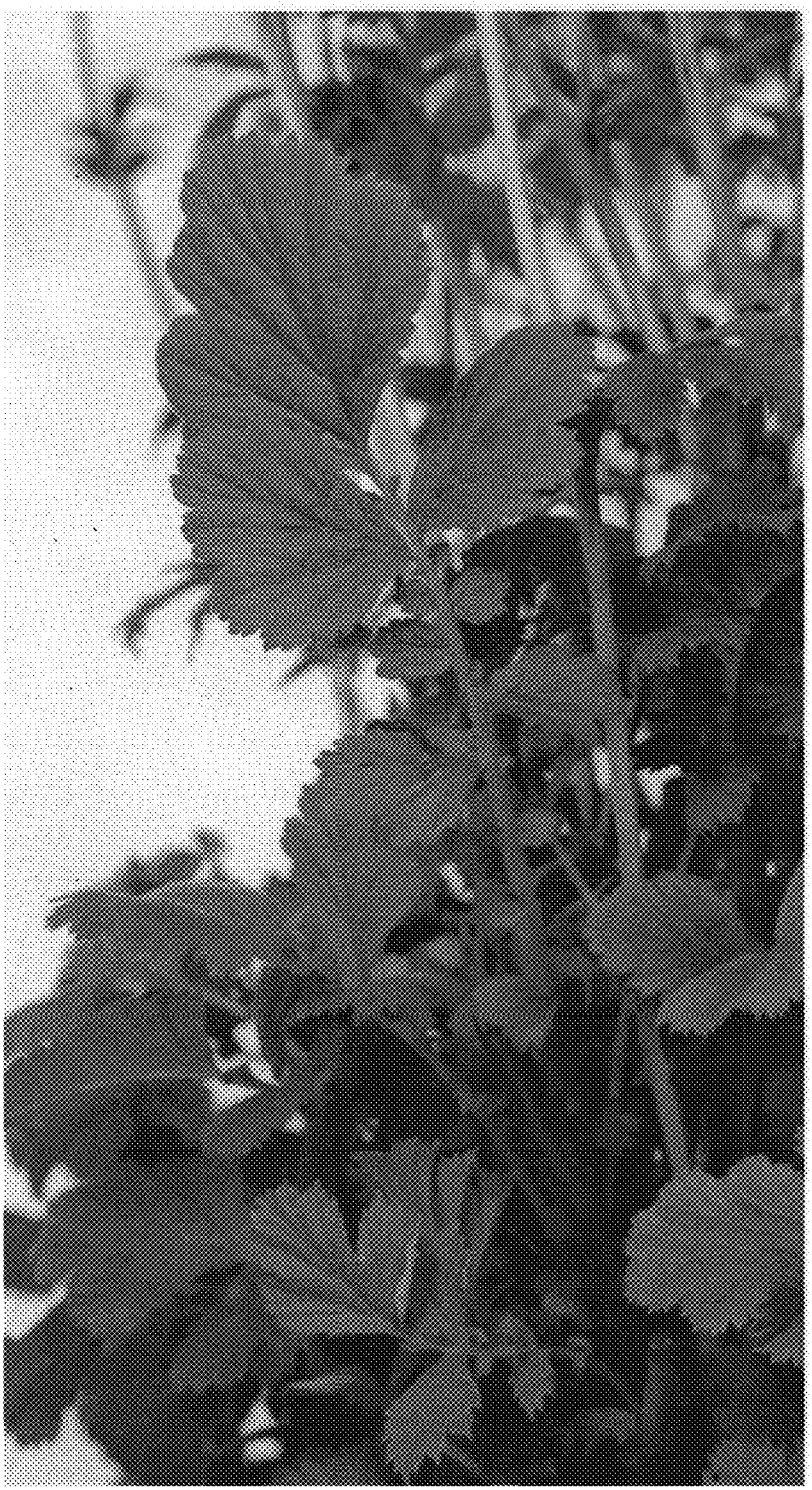
FIG. 2 shows, as nearly true as it is reasonably possible to make the same in color illustrations of this type, the typical foliage of the plant in FIG. 1.
Figure 3:
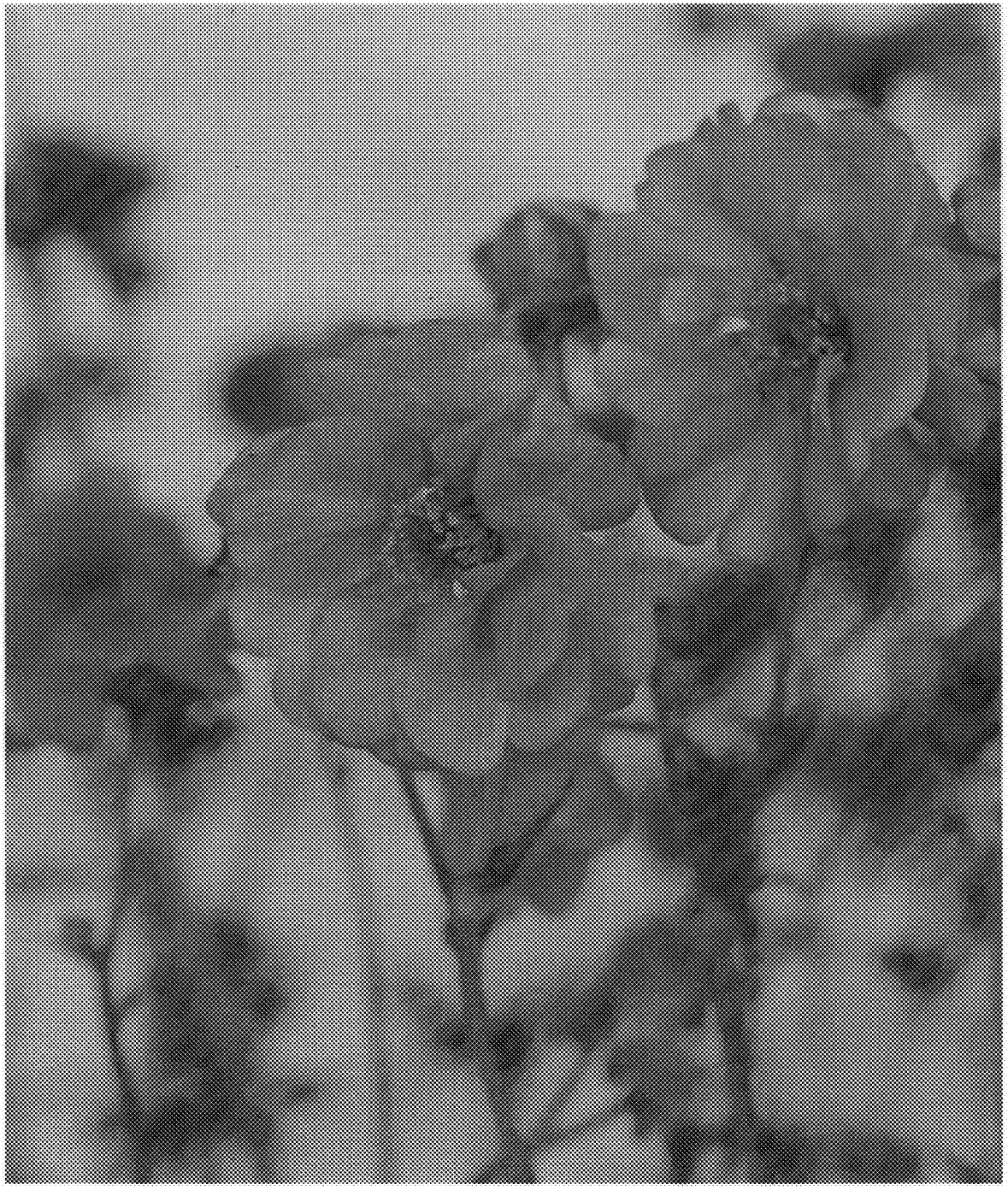
FIG. 3 shows, as nearly true as it is reasonably possible to make the same in color illustrations of this type, the typical flower of the plant in FIG. 1.

The following is a detailed botanical description of a new and distinct variety of *Geum* known as 'MACGEU007', based upon observations of 4.5-month-old plants grown outdoors in Kirkcudbright, Scotland. Plants were grown with full sun to partial shade exposure and subsisted on natural rainfall with supplemental irrigation provided during periods of dry weather. Plants were grown in a nutrient-rich compost but were otherwise not given any supplemental fertilizer. No chemical pest treatments were given to the plants. Observation data was recorded in May of 2021.

Those skilled in the art will appreciate that certain characteristics will vary with older or, conversely, with younger plants. 'MACGEU007' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'MACGEU007' and comparisons with the parents and most similar variety of common knowledge are provided below.

General plant description:

*Growth habit.*—Herbaceous perennial with no lateral branching, flowering stems arising from the base, and inflorescence held above the foliar plane.

*Plant profile.*—Broad vase-shaped.

*Height.*—64.8 cm to the top of the foliar plane; 80.8 cm to the top of the floral plane.

*Spread.*—92.8 cm.

*Plant vigor.*—Very vigorous.

*Growth rate.*—Fast-growing to very fast-growing.

*Propagation.*—Method — Meristematic tissue culture. Time to initiate rooting — 12 days at an average ambient temperature of 22 degrees Celsius. Time to produce flowering plant from rooted cutting — Approximately 4 months in a 15 cm container; 6 months in a 17 cm container.

*Pest resistance and susceptibility.*—Not any more or less susceptible to pests or diseases known to effect *Geum*.

*Environmental tolerances.*—Adapt to, at least, USDA Zones 5 to 9 and temperatures ranging from minus 25 degrees Celsius to 35 degrees Celsius; low to moderate tolerance to rain; moderate to high tolerance to wind.

Root system: Thin, fibrous, and freely branched.

Stem:

*Branching habit.*—Basally branched; free branching.

*Number of primary (main) stems per plant.*—50.

*Number of secondary (lateral) branches per plant.*—None.

*Attitude.*—Average angle of 30 degrees from vertical; stems vary from between 0 to 60 degrees from vertical.

*Aspect.*—Rounded.

*Length.*—51.6 cm.

*Diameter.*—0.4 cm.

*Internode length.*—9.6 cm.

*Texture.*—Moderately pubescent; hairs are soft, white RHS N155A, and 0.1 cm long, on average.

*Luster.*—Moderately glossy.

*Strength.*—Strong.

*Color, juvenile.*—Yellow-green, nearest to RHS 144B.

*Color, mature.*—Yellow-green, nearest to RHS 144A.

*Color at internodes.*—Yellow-green, nearest to RHS 144A.

Foliage:

*Arrangement.*—Leaves are borne both basally and on stems; on stems, arrangement is alternate.

*Basal leaves.*—Attachment — Petiolate. Division — Simple. Shape — Lyrate. Dimensions — 31.6 cm long, including petiole, and 6.7 cm wide. Attitude — Upward and outward. Aspect — Slightly curled downward. Apex — Praemorse. Base — Broad acuminate. Margin — Serrate to biserrate. Texture, adaxial and abaxial surfaces — Smooth, pubescent. Pubescence, adaxial and abaxial surfaces — Moderately covered with soft, strigose hairs with an average length of 0.075 cm; colored white, nearest to RHS N155A. Luster, adaxial surface — Matte. Luster, abaxial surface — Slightly glossy. Color — Juvenile color, adaxial surface — Green, nearest to RHS 137C. Juvenile color, abaxial surface — Yellow-green, nearest to RHS 146B. Mature color, adaxial surface — Green, nearest to RHS 143A. Mature color, abaxial surface — Yellow-green, nearest to RHS 146B. Venation — Type — Pinnate. Vein color, adaxial surface — Green, nearest to RHS 143A. Vein color, abaxial surface — Yellow-green, nearest to RHS 144C. Petiole — Length — 25.7 cm. Diameter — 0.2 cm. Strength — Moderately strong. Texture, adaxial and abaxial surfaces — Densely covered with soft hairs; average length of hairs is 0.075 cm; colored white, nearest to RHS N155A. Luster, adaxial and abaxial surfaces — Slightly glossy. Color, adaxial surface — Yellow-green, nearest to a mixture of RHS 144A and 144B. Color, abaxial surface — Yellow-green, nearest to RHS 145A. Stipules — None present.

*Leaves borne on the stems.*—Quantity — Approximately 6 leaves per stem. Attachment — Petiolate. Division — Simple. Shape — Lyrate to trilobate; lobes are deeply lobed to near-cleft. Lobes — Depth of sinuses — Deep. Sinus orientation — Divergent. Dimensions — 6.5 cm long, excluding the petiole, and 4.5 cm wide. Attitude — Leaves in an average angle of 50 degrees to the stem. Aspect — Slightly curled downward. Apex — Narrow acute. Base — Broad acuminate. Margin — Coarsely serrate to incised. Texture, adaxial and abaxial surfaces — Smooth, pubescent. Pubescence, adaxial and abaxial surfaces — Moderately covered with soft, strigose hairs with an average length of 0.075 cm; colored white, nearest to RHS N155A. Luster, adaxial surface — Matte. Luster, abaxial surface — Slightly glossy. Color — Juvenile color, adaxial surface — Green, nearest to RHS 137C. Juvenile color, abaxial surface — Yellow-green, nearest to RHS 146B. Mature color, adaxial surface — Green, nearest to RHS 137A. Mature color, abaxial surface — Yellow-green, nearest to RHS 146B. Venation — . Type — Pinnate. Vein color, adaxial surface — Green, nearest to RHS 137A. Vein color, abaxial surface — Yellow-green, nearest to RHS 145A. Petiole — Length — 2.4 cm. Diameter — 0.15 cm. Strength — Moderately strong. Texture, adaxial and abaxial surfaces — Densely covered with soft hairs; average length of hairs is 0.075 cm; colored white, nearest to RHS N155A. Luster, adaxial and abaxial surfaces — Slightly glossy. Color, adaxial surface — Yellow-green, nearest to RHS 144B. Color, abaxial surface — Yellow-green, nearest to RHS 146D. Stipules — General — Two leafy stipules present at the base of each leaf. Shape — Broad ovate. Length — 2.4 cm.. Diameter — 1.6 cm. Apex — Incised. Base — Cuneate. Margins — Serrate. Texture, adaxial and abaxial surfaces — Densely covered with soft hairs; average length of hairs is 0.1 cm; colored white, RHS N155A. Luster, adaxial and abaxial surfaces — Moderately glossy. Color, adaxial surface — Green, nearest to RHS 137A. Color, abaxial surface — Yellow-green, nearest to RHS 146B.

Inflorescence:

*Habit.*—Compound cyme.

*Natural flowering season.*—Spring into summer in Kirkcudbright, Scotland.

*Time to flower or response time.*—Approximately 9 months.

*Dimensions.*—23.9 cm high, from lowest cauline petiole, and 14.2 cm in diameter.

*Quantity of inflorescence per plant.*—36, on average.

*Quantity of flowers per inflorescence.*—11, on average.

*Quantity of flower buds per plant.*—Approximately 150.

*Quantity of flowers per plant.*—Approximately 400.

*Quantity of flowers and flower buds per plant.*—550, on average.

*Peduncles.*—Length — Average of 16.0 cm. Diameter — Average of 0.3 cm. Angle — Average angle to stem is 25 degrees. Strength — Moderately strong to strong. Texture — Smooth and moderately pubescent; hairs are soft with an average length of 0.05 cm; colored white, nearest to RHS N155A. Luster — Slightly glossy. Color— Yellow-green, nearest to RHS 146C.

Flower buds:

*Shape.*—Broad oblong to flattened globular.

*Length.*—1.1 cm.

*Diameter.*—1.1 cm.

*Texture.*—Smooth and moderately pubescent; hairs are soft with an average length of 0.075 cm; colored white, nearest to RHS N155A.

*Luster.*—Matte.

*Color.*—Yellow-green, nearest to RHS 144A, and suffused darker, nearest to RHS 146B; emerging flower petals are yellow-green, nearest to RHS 154C and suffused with orange-red, nearest to RHS 34C.

Flower:

*Shape, type.*—Rotate; semi-double.

*Flowering habit.*—Very freely flowering.

*Aspect.*—Upright to outward.

*Flower longevity on plant.*—Approximately ten days.

*Persistent or self-cleaning.*—Self-cleaning.

*Fragrance.*—Non-fragrant.

*Diameter.*—4.7 cm.

*Depth.*—2.8 cm.

*Pedicels.*—Length — 4.1 cm. Diameter — 0.175 cm. Attitude — At an average angle of 35 degrees to the peduncle. Strength — Moderately strong. Texture — Smooth and moderately pubescent; hairs are soft with an average length of 0.05 cm; colored light orange-red, nearest to RHS RHS 33B. Luster — Slightly glossy. Color — Yellow-green, nearest to RHS 144A.

*Calyx.*—Shape — Rotate. Length — 1.2 cm. Diameter — 2.4 cm. Sepals — Arrangement — Rotate; one whorl of sepals which alternate between broad sepals and narrow sepals. Quantity— 10 unfused sepals; 5 broad sepals and 5 narrow sepals. Broad sepals — Shape — Deltoid. Dimensions — 1.3 cm long and 0.7 cm wide. Apex — Acute. Base — Straight. Sepal reflex — Strongly reflexed. Margin — Entire; pubescent. Texture, upper surface — Smooth and sparsely to moderately pubescent; hairs are soft with an average length of 0.05 cm; colored white, nearest to RHS N155A. Texture, lower surface — Smooth, moderately covered with soft strigose hairs, and very slightly glossy; hairs are approximately 0.075 cm long and colored white, nearest to RHS N155A. Luster, upper surface — Very slightly glossy. Luster, lower surface — Very slightly glossy. Color — When opening, upper surface — Yellow-green, nearest to RHS 144B; tipped brown, nearest to RHS 200A. When opening, lower surface — Yellow-green, nearest to RHS 144B; tipped brown, nearest to RHS 200A. Fully opened, upper surface — Yellow-green, nearest to RHS 144B; tipped brown, nearest to RHS 200A. Fully opened, lower surface — Yellow-green, nearest to RHS 145A; tipped brown, nearest to RHS 200A. Narrow sepals — Shape — Lanceolate to narrow elliptic. Dimensions — 0.6 cm long and 0.15 cm wide. Apex — Narrowly acute. Base — Attenuate. Sepal reflex — Very slightly reflexed. Margin — Entire. Texture, upper surface — Smooth and sparsely to moderately pubescent; hairs are soft with an average length of 0.05 cm; colored white, nearest to RHS N155A. Texture, lower surface — Smooth, moderately covered with soft strigose hairs, and very slightly glossy; hairs are approximately 0.075 cm long and colored white, nearest to RHS N155A. Luster, upper surface — Very slightly glossy. Luster, lower surface — Very slightly glossy. Color — When opening, upper surface — Yellow-green, nearest to RHS 144B; tipped brown, nearest to RHS 200A. When opening, lower surface — Yellow-green, nearest to RHS 144B; tipped brown, nearest to RHS 200A. Fully opened, upper surface — Yellow-green, nearest to RHS 144B; tipped brown, nearest to RHS 200A. Fully opened, lower surface — Yellow-green, nearest to RHS 145A; tipped brown, nearest to RHS 200A.

*Petals.*—Quantity — 20, on average; varying from 15 to 25. Arrangement — Rotate; arranged in four whorls of unfused petals. Length — 1.8 cm. Width — 2.0 cm. Shape — Reniform to broad obovate. Apex — Variable; broad emarginate to retuse and obtuse. Base — Broad attenuate to truncate. Margin — Entire; moderate to high undulation. Texture, upper surface — Glabrous, slightly velvety and matte. Texture, lower surface — Glabrous, smooth, and matte. Petal color — When opening, upper surface — Marbled with a combination of orange and orange-red, nearest to RHS 28A, 28B, and 33B. When opening, lower surface — Yellow-orange, nearest to RHS 22A, and becoming orange-red towards the margins and apex, nearest to RHS 31B. Fully opened, upper surface — Orange-red, nearest to RHS N30C, and slightly lighter at the center, nearest to RHS N30D; darker towards the margins and apex, nearest to a mixture of RHS N30A and N30B. Fully opened, lower surface — Orange, nearest to RHS 26A, and becoming orange-red towards the margins and apex, nearest to a mixture of RHS 31A and 31B. When faded, upper surface — Orange-red, nearest to RHS 33B. When faded, upper surface — Orange-red, nearest to a mixture of RHS 30A and 30B. Petal venation color — Fully opened, upper surface — Orange-red; nearest to RHS N30A. Fully opened, lower surface — Orange; nearest to RHS 26A, yet slightly darker.

Reproductive organs:

*Androecium.*—Stamens — Quantity — Approximately 140. Anthers — Attachment — Dorsifixed. Shape — Oblong. Dimensions — 0.1 cm long and 0.05 cm wide. Color — Yellow, nearest to a mixture of RHS 9B and 9C. Filaments — Length — 0.6 cm. Color — Yellow-orange, nearest to RHS 23B, and fading to yellow towards the base, nearest to RHS 12A. Amount of Pollen — Sparse. Pollen color — Yellow, nearest to RHS 12A.

*Gynoecium.*—Pistil — Quantity — 50, on average. Length — 0.5 cm. Style — Length — 0.45 cm. Color — Orange, RHS 24A. Stigma — Shape — Cleft; two-parted. Length — 0.05 cm. Diameter — 0.05 cm. Color — Red, RHS 42A. Ovary Color — Yellow-green, nearest to a mixture of RHS 145A and 145B.

Seed and fruit: No fruit or seeds have been detected to date.

Comparisons with the parent plants: Plants of the new cultivar 'MACGEU007' differ from its seed parent, *Geum chiloense* 'Blazing Sunset' (unpatented), by the characteristics described in Table 1.

TABLE 1

| Characteristic | 'MACGEU007' | 'Blazing Sunset' |
|---|---|---|
| Flower conformation. | Semi-doubled. | Doubled. |
| General coloration of the flower. | Orange. | Red. |
| Bloom period. | Longer than 'Blazing Sunset'. | Shorter than 'MACGEU007'. |

Plants of the new cultivar 'MACGEU007' may be distinguished from its pollen parent, *Geum coccineum* 'Eos Hybrid No. 1' (unpatented), by the characteristics described in Table 2.

TABLE 2

| Characteristic | 'MACGEU007' | 'Eos Hybrid No. 1' |
|---|---|---|
| Flower conformation. | Semi-doubled. | Single. |
| General coloration of the flower. | Orange. | A mixture of peach and pink. |
| Bloom period. | Longer than 'Eos Hybrid No. 1'. | Shorter than 'MACGEU007'. |

Comparison with the most similar variety of common knowledge: Plants of the new cultivar 'MACGEU007' may be distinguished from the most similar known commercial comparator, *Geum* 'MACGEU001' (U.S. Plant Pat. No. 28,476), by the characteristics described in Table 3.

TABLE 3

| Characteristic | 'MACGEU007' | 'MACGEU001' |
|---|---|---|
| Abundance of flowers. | More abundant than 'MACGEU001'. | Less abundant than 'MACGEU007'. |
| Flower petal quantity. | More petals than 'MACGEU001'. | Fewer petals than 'MACGEU007'. |
| General coloration of the flower. | Orange. | Orange-red. |

That which is claimed is:

1. A new and distinct variety of *Geum* hybrid plant named 'MACGEU007', substantially as described and illustrated herein.

* * * * *